United States Patent
Jensen et al.

(10) Patent No.: US 8,058,498 B2
(45) Date of Patent: Nov. 15, 2011

(54) DEVICE FOR REMOVING OXYGEN-CONTAINING ORGANIC COMPOUNDS FROM MIXTURES OF VARIOUS HYDROCARBON COMPOUNDS

(76) Inventors: Sandra Jensen, Frankfurt am Main (DE); Martin Rothaemel, Frankfurt am Main (DE); Harald Koempel, Neu-Isenburg (DE); Herrmann Bach, Heiligenroth (DE); Gerhard Birke, Frankfurt am Main (DE)

( * ) Notice: Subject to any disclaimer, the term of this patent is extended or adjusted under 35 U.S.C. 154(b) by 441 days.

(21) Appl. No.: 11/718,020

(22) PCT Filed: Oct. 11, 2004

(86) PCT No.: PCT/EP2005/010921
§ 371 (c)(1),
(2), (4) Date: Apr. 26, 2007

(87) PCT Pub. No.: WO2006/048098
PCT Pub. Date: May 11, 2006

(65) Prior Publication Data
US 2009/0223870 A1    Sep. 10, 2009

(30) Foreign Application Priority Data
Oct. 29, 2004 (DE) .................... 10 2004 052 658

(51) Int. Cl.
*C07C 7/08* (2006.01)
(52) U.S. Cl. ........ 585/809; 585/802; 585/833; 585/834; 585/860; 585/862; 585/864; 208/236; 208/237; 208/263; 208/339; 208/412
(58) Field of Classification Search .......... 585/809, 585/802, 834, 860, 862, 864, 833; 208/263, 208/339, 236, 237, 412
See application file for complete search history.

(56) References Cited

U.S. PATENT DOCUMENTS

| | | | | |
|---|---|---|---|---|
| 4,587,373 A | * | 5/1986 | Hsia | 585/639 |
| 6,483,000 B2 | * | 11/2002 | Becker | 585/800 |
| 6,653,044 B2 | * | 11/2003 | Takeda et al. | 430/270.1 |
| 6,864,401 B2 | * | 3/2005 | Van Egmond | 585/639 |
| 7,005,555 B2 | * | 2/2006 | Ding et al. | 585/638 |
| 7,060,865 B2 | * | 6/2006 | Ding et al. | 585/800 |
| 2003/0004386 A1 | * | 1/2003 | Lattner et al. | 585/804 |

(Continued)

FOREIGN PATENT DOCUMENTS

| | | |
|---|---|---|
| WO | 03/020671 | 3/2003 |
| WO | 03/020672 | 3/2003 |
| WO | 03/020678 | 3/2003 |

*Primary Examiner* — Walter Griffin
*Assistant Examiner* — Huy-Tram Nguyen
(74) *Attorney, Agent, or Firm* — Norris McLaughlin & Marcus P.A.

(57) ABSTRACT

Process for removing oxygen-containing organic compounds from mixtures of hydrocarbon compounds, in which a liquid phase (1) containing hydrocarbons and oxygenates is charged to a first column (3), a light fraction is separated as top product (5) by distillation, and that a heavier C4+ fraction is removed from the bottom, the light fraction (5) and a gaseous mixture of hydrocarbons and oxygenates (2) is charged to a second column (7), and separated into a light and a heavy hydrocarbon fraction distillation, and an additional solvent (6) is supplied to the upper part of the second column (7), which dissolves the oxygenates and, the solvent and oxygenates being discharged as bottom product (9) and a hydrocarbon product (8), which is free from oxygenates leaves the top of the column (7). The solvent optionally is wholly or partly regenerated and recirculated to the extractive distillation column.

11 Claims, 1 Drawing Sheet

Hsia-Scheme (numbers refer to the figures in the Patent)

U.S. PATENT DOCUMENTS

2003/0045655 A1* 3/2003 Hendriksen et al. ............ 526/77
2003/0199724 A1* 10/2003 Van Egmond et al. ....... 585/899
2004/0064002 A1* 4/2004 Lee et al. ..................... 568/698
2004/0176646 A1* 9/2004 Van Egmond et al. ....... 568/699
2004/0267069 A1* 12/2004 Ding et al. .................... 585/329
2006/0211907 A1* 9/2006 Pieter de Wet et al. ....... 585/864

* cited by examiner

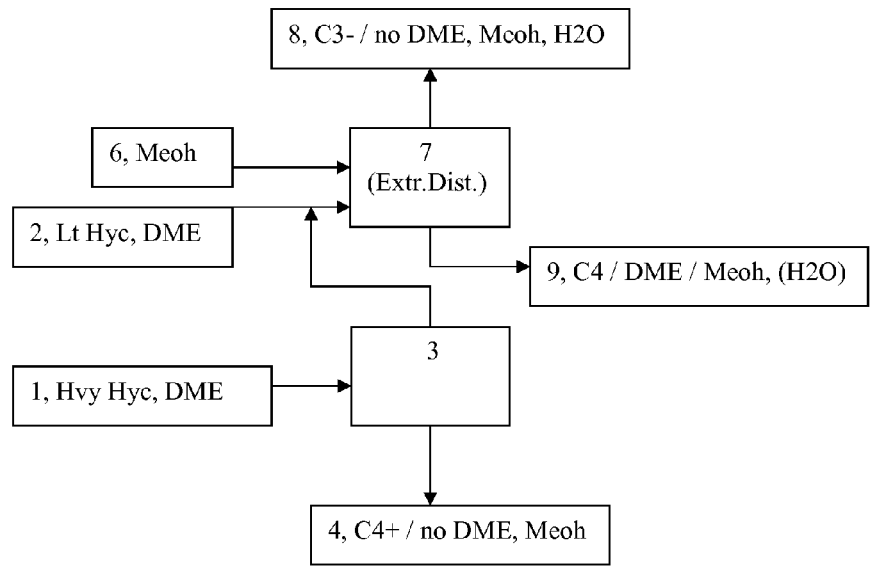
fig. 1: US 11/718,020 (numbers refer to the figures in the Patent Application)
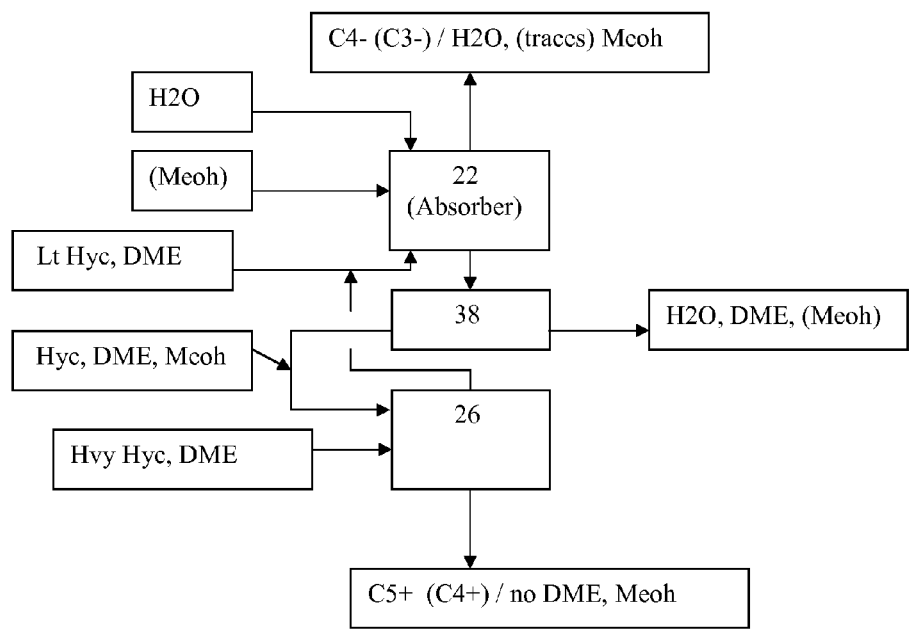
fig. 2: Hsia-Scheme (numbers refer to the figures in the Patent)

DEVICE FOR REMOVING OXYGEN-CONTAINING ORGANIC COMPOUNDS FROM MIXTURES OF VARIOUS HYDROCARBON COMPOUNDS

This is a 371 of PCT/EP2005/010921 filed 11 Oct. 2005 (international filing date).

This invention relates to a process for removing oxygen-containing organic compounds (oxygenates) from mixtures of various hydrocarbon compounds by simultaneously separating the hydrocarbon compounds into individual fractions.

BACKGROUND OF THE INVENTION

Hydrocarbon compounds are basic elements of the chemical industry and starting substances for a multitude of products. Industrially useful hydrocarbon compounds can be produced by converting solid, liquid or gaseous fossil fuels. An example for this is the increased utilization of natural gas for the production of liquid fuels and chemicals. Natural gas can for instance be converted to synthesis gas, and synthesis gas can be used for producing hydrogen, for instance for use in refineries and fuel cells, for producing Fischer-Tropsch products, such as sulfur-free fuels, lubricants, waxes and α-olefins, for producing DME, for instance for use in gas turbines and fuel cells, and especially for producing methanol as starting substance for the recovery of formaldehyde, solvent, methyl-tert-butyl ether, synthetic fuels, acetic acid, olefins, etc.

In the primary production processes, the hydrocarbon compounds typically are obtained in the form of mixtures which must be separated into individual fractions or pure substances by means of separation processes—above all fractionated distillation. The interconnection of the separation apparatuses used in the conventional processes leads to large dimensions of the individual equipment parts as well as to a high specific consumption of resources. Accordingly, the optimum configuration of the separation process is of great importance. The hydrocarbon compounds should be produced as pure as possible without the presence of oxygen-containing organic compounds (oxygenates). Oxygenates are understood to be compounds with at least one hydrocarbon backbone and a low content of oxygen.

In accordance with the prior art, the oxygenates were separated by a classically connected distillation or a physical washing of hydrocarbon compounds. In particular in the case of industrial production plants, however, this is very complex and expensive. In the references WO 03/020671, WO 03/020672 and WO 03/020678 processes for the extractive distillation of olefins are described.

SUMMARY OF THE INVENTION

It is the object of the present invention to provide a process for removing oxygen-containing organic compounds (oxygenates) from mixtures of various hydrocarbon compounds with a carbon number (C number) from C-1 to C-9, in which the remaining amount of the oxygenates in the main-value product stream, e.g. an olefin stream, is reduced to below 1 ppm and a separation into partial fractions is achieved, while at the same time minimizing the apparatus dimensions and the specific consumption of resources.

This object is solved in that the mixture of hydrocarbons and oxygen-containing organic compounds is processed in a two-stage separation process. Typically, such hydrocarbon streams—e.g. after a compression—are present in a two-phase form, the heavier hydrocarbons being in the liquid phase. In the present invention, these two phases are not charged together into one distillation column, as it is done conventionally, but each separately into two distillation columns. In the first column, a light fraction is separated from the liquid phase, which light fraction contains the main-value product and oxygenates.

The gas phase is charged into the second column together with the light fraction of the first column. This second column is an extractive distillation column. The mixture is separated into a light and a heavy hydrocarbon cut. A solvent which dissolves the oxygenates is supplied into the upper part of the column. Thus, the content of oxygenates is decreased distinctly as compared to the prior art.

Due to the effect of the solvent, the oxygenates contained in the hydrocarbon stream are removed by extraction and get into the bottom of the column.

A product free from oxygenates leaves the top of the column. At the bottom, the oxygenates, the solvent and the hydrocarbons not belonging to the product are withdrawn. By product free from oxygenates a product is meant which has a content of oxygen-containing organic compounds <1 ppm. The column is operated at a pressure of 5 to 35 bar.

DETAILED DESCRIPTION

As solvent, mono-alcohols or di-alcohols can be used in general. Methanol, diethylene glycol, ethanol or propanol are particularly useful. Alternatively, there can also be used N-methylpyrrolidone (NMP) with and without addition of water.

As hydrocarbons, there can be used olefins (mono- or diolefins), paraffins, naphthenes or aromatics or a mixture of these substances. These hydrocarbons can originate e.g. from a catalytic reaction process.

The oxygen-containing organic compounds can be present as ether such as e.g. dimethyl ether (DME), ester such as e.g. methyl formate, ketones such as e.g. methyl ethyl ketone, or aldehydes such as e.g. formaldehyde. In a simple case, the solvent, e.g. methanol (MeOH), is used in the process as starting substance of the product synthesis, so that a direct recirculation of the solvent together with the dissolved oxygenates and hydrocarbons into the process is possible. If this is not possible or unfavorable for technical or economic reasons, or if the solvent NMP is used instead of alcohols, the solvent can be separated from the oxygenates and hydrocarbons by a separation process, e.g. extraction or distillation, and partly or completely be recirculated to the extractive distillation column.

BRIEF DESCRIPTION OF THE DRAWINGS

FIG. 1 illustrates the process of the invention, wherein a liquid fraction (1) is charged to column (3) which separates low-boiling components (5) from higher-boiling components (4). The low-boiling components (5) and gas phase (2) are charged to extractive distillation column (7).

FIG. 2 illustrates the process configuration shown in FIG. 1, but further including a solvent-regeneration column (10).

The invention is represented in the drawings (FIG. 1, FIG. 2) by a process example—the production of a C3 hydrocarbon stream free from oxygenates from a mixture of C1-C8 hydrocarbons and oxygenates, in particular DME–, which will be explained below.

A liquid fraction (1) of hydrocarbons and oxygenates is charged into a first column (3). The same separates low-boiling components C4− and DME (5) from C4+ hydrocarbons (4). The fraction with C4+hydrocarbons (4) is supplied to a non-illustrated distillation column, in which light naphtha product (C4-C6) is separated from C7+ gasoline product (paraffins, olefins, naphthenes and aromatics).

The gaseous fraction (2), consisting of mostly C3 hydrocarbons, but also residual amounts of C4 hydrocarbons as well as oxygenates, and the C4− top product of the first column (5) are supplied to an extractive distillation in a second column (7). The second column (7) separates this mixture at a pressure of 21 to 25 bar into a light and a heavy hydrocarbon cut. To prevent oxygenates from getting into the top product as impurity, a liquid solvent is used. This solvent is supplied to the column (7) via conduit (6). In this example, methanol is used as solvent. By means of the solvent, the oxygenates contained in the hydrocarbon stream are removed by extraction, get into the bottom of the column (7) and are withdrawn via conduit (9). A product free from oxygenates leaves the top of the column (7) via conduit (8), which product can be processed in further non-illustrated distillation columns to obtain e.g. pure polymerizable propylene.

In a simple case (FIG. 1, Example 1) it is assumed that the mixture of hydrocarbons/oxygenates/methanol withdrawn via conduit (9) can be used as starting material in the basic process. Therefore, there is no need for regenerating the solvent.

In Example 2 (FIG. 2), there is shown a process configuration with a regeneration of the solvent. The same is required when the solvent methanol cannot be used in the basic process, or only to a limited extent. In this diagram, the mixture withdrawn via conduit (9) is supplied to the column (10). The top product (12) contains the light fraction consisting of hydrocarbons as well as oxygenates, in particular DME. This mixture (12) can directly be supplied as starting material to the product synthesis of the non-illustrated basic process. The bottom product is withdrawn via conduit (11) and contains the regenerated solvent as well as water, which is introduced as byproduct via the streams (1) and (2). The larger part of this stream is supplied to the extractive distillation column (7) via conduit (14). A smaller part of the stream is supplied via conduit (13) to a further processing, e.g. in a distillation column, in order to separate methanol and further oxygenates from waste water. The mass flow (13) is adjusted such that in the extractive distillation column (7) the water content in the liquid phase is 0.5 to 2 wt-%, preferably 1 wt-%, and thus the occurrence of a second liquid phase in the column is prevented.

In Example 3 (FIG. 2), a mixture of NMP (87.5 wt-%) and water (12.5 wt-%) is used as solvent. In this case, the water content of 12.5 wt-% is adjusted directly via the bottom temperature due to the high boiling point of the solvent in the bottom of the column (10), the solvent is regenerated completely and supplied to the extractive distillation column (7) via conduit (14). In the case of a contamination of the solvent—e.g. by polymerization—, a small amount of (11) is discontinuously removed from the circuit via conduit (13). In this case, a small amount of fresh NMP is supplied as substitute via conduit (6).

EXAMPLE 1

Configuration without solvent regeneration, with methanol as solvent

| | Stream number | | | | | | |
|---|---|---|---|---|---|---|---|
| Mass flow rate kg/hr | 1 | 2 | 4 | 5 | 6 | 8 | 9 |
| MeOH | 408.2 | 98.9 | 0.0 | 408.2 | 30000.0 | 0.1 | 30507.0 |
| DME | 697.2 | 407.1 | 0.0 | 697.1 | 0.0 | 0.1 | 1104.2 |
| H2O | 765.5 | 161.8 | 0.0 | 765.4 | 0.0 | 0.0 | 927.3 |
| C2H4 | 3819.6 | 8908.9 | 0.0 | 3818.6 | 0.0 | 12727.6 | 0.0 |
| C3H6 | 34975.6 | 25857.1 | 30.9 | 34940.8 | 0.0 | 60425.2 | 372.6 |
| 1-C4H8 | 7306.4 | 1440.0 | 3259.7 | 4046.7 | 0.0 | 0.0 | 5486.7 |
| C—C4H8 | 7541.2 | 963.3 | 5477.1 | 2064.2 | 0.0 | 0.0 | 3027.5 |
| T-C4H8 | 7483.5 | 1081.7 | 4876.1 | 2607.4 | 0.0 | 0.0 | 3689.1 |
| I—C4H8 | 7177.3 | 1416.4 | 3337.5 | 3839.6 | 0.0 | 0.0 | 5256.0 |
| C5H10 | 13626.8 | 266.3 | 13615.8 | 11.0 | 0.0 | 0.0 | 277.3 |
| Olefins C6-C8 | 10861.3 | 18.1 | 10861.3 | 0.0 | 0.0 | 0.0 | 18.1 |
| C2H6 | 144.0 | 271.7 | 0.0 | 143.9 | 0.0 | 415.7 | 0.0 |
| C3H8 | 549.3 | 360.4 | 1.6 | 547.6 | 0.0 | 901.0 | 7.0 |
| N—C4H10 | 23478.5 | 4035.9 | 14027.3 | 9449.4 | 0.0 | 0.0 | 13485.2 |
| I—C4H10 | 33454.3 | 7623.1 | 13566.5 | 19886.1 | 0.0 | 0.0 | 27509.3 |
| C5H12 | 55893.0 | 1272.8 | 55827.8 | 65.1 | 0.0 | 0.0 | 1337.9 |
| Paraffins C6-C8 | 18342.2 | 27.7 | 18342.2 | 0.0 | 0.0 | 0.0 | 27.7 |
| Alcohols C2-C5 | 297.8 | 0.1 | 297.8 | 0.0 | 0.0 | 0.0 | 0.1 |
| Naphthenes C5-C6 | 6203.3 | 4.1 | 6203.3 | 0.0 | 0.0 | 0.0 | 4.1 |
| Aromatics | 4277.7 | 0.3 | 4277.7 | 0.0 | 0.0 | 0.0 | 0.3 |
| Ketones C3-C5 | 396.1 | 1.4 | 396.1 | 0.0 | 0.0 | 0.0 | 1.4 |
| Aldehydes C1-C3 | 266.3 | 30.7 | 184.4 | 81.9 | 0.0 | 0.0 | 112.6 |
| Methyl formate | 94.9 | 2.6 | 94.8 | 0.0 | 0.0 | 0.0 | 2.7 |
| H2 + CH4 | 505.0 | 3552.5 | 0.0 | 503.6 | 0.0 | 4056.2 | 0.0 |
| Mass flow rate kg/hr | 238565.0 | 57803.0 | 154678.0 | 83876.8 | 30000.0 | 78525.7 | 93154.2 |
| Temperature ° C. | 100.0 | 77.4 | 161.4 | 44.6 | 20.0 | 36.8 | 103.1 |
| Pressure bar | 24.6 | 22.0 | 22.0 | 21.7 | 10.0 | 21.5 | 22.0 |
| Density kg/m³ | 495.0 | 36.0 | 439.7 | 505.4 | 790.8 | 39.8 | 534.5 |
| Molar wt. kg/kmol | 59.4 | 39.6 | 70.0 | 46.4 | 32.0 | 36.9 | 44.8 |

EXAMPLE 2

Configuration with solvent regeneration and circulation, with methanol as solvent

| Mass flow rate kg/hr | Stream number | | | | | | |
|---|---|---|---|---|---|---|---|
| | 1 | 2 | 4 | 5 | 6 | 8 | 9 |
| MeOH | 423.2 | 83.9 | 0.0 | 423.2 | 8802.5 | 0.2 | 30506.6 |
| DME | 740.3 | 364.0 | 0.0 | 740.2 | 0.0 | 0.1 | 1104.2 |
| H2O | 798.6 | 128.7 | 0.0 | 798.6 | 0.0 | 0.0 | 3139.6 |
| C2H4 | 4218.1 | 8510.4 | 0.0 | 4217.1 | 0.0 | 12727.5 | 0.0 |
| C3H6 | 37257.5 | 23575.3 | 32.4 | 37221.1 | 0.0 | 60437.8 | 358.5 |
| 1-C4H8 | 7565.4 | 1181.1 | 3774.4 | 3790.9 | 0.0 | 0.0 | 4971.9 |
| C—C4H8 | 7753.3 | 751.3 | 6233.8 | 1519.4 | 0.0 | 0.0 | 2270.8 |
| T-C4H8 | 7709.1 | 856.1 | 5622.4 | 2086.7 | 0.0 | 0.0 | 2942.8 |
| I—C4H8 | 7431.8 | 1162.0 | 3864.1 | 3567.5 | 0.0 | 0.0 | 4729.5 |
| C5H10 | 13733.2 | 159.9 | 13729.2 | 3.9 | 0.0 | 0.0 | 442.7 |
| Olefins C6-C8 | 10872.2 | 7.2 | 10872.2 | 0.0 | 0.0 | 0.0 | 28.8 |
| C2H6 | 158.1 | 257.6 | 0.0 | 158.1 | 0.0 | 415.6 | 0.0 |
| C3H8 | 583.5 | 326.1 | 2.0 | 581.5 | 0.0 | 903.1 | 4.5 |
| N—C4H10 | 24211.6 | 3302.7 | 16243.3 | 7968.0 | 0.0 | 0.0 | 11270.7 |
| I—C4H10 | 34755.4 | 6322.1 | 15426.6 | 19327.9 | 0.0 | 0.0 | 25650.0 |
| C5H12 | 56378.2 | 787.5 | 56355.0 | 23.2 | 0.0 | 0.0 | 1730.9 |
| Paraffins C6-C8 | 18358.9 | 11.0 | 18358.9 | 0.0 | 0.0 | 0.0 | 44.0 |
| Alcohols C2-C5 | 297.9 | 0.1 | 297.9 | 0.0 | 0.0 | 0.0 | 0.2 |
| Naphthenes C5-C6 | 6206.2 | 1.3 | 6206.2 | 0.0 | 0.0 | 0.0 | 5.2 |
| Aromatics | 4277.8 | 0.1 | 4277.8 | 0.0 | 0.0 | 0.0 | 0.4 |
| Ketones C3-C5 | 396.8 | 0.8 | 396.8 | 0.0 | 0.0 | 0.0 | 3.1 |
| Aldehydes C1-C3 | 271.7 | 25.3 | 190.9 | 80.8 | 0.0 | 0.0 | 424.4 |
| Methyl formate | 95.8 | 1.7 | 95.8 | 0.0 | 0.0 | 0.0 | 7.0 |
| H2 + CH4 | 553.2 | 3504.3 | 0.0 | 551.7 | 0.0 | 4056.0 | 0.0 |
| Mass flow rate kg/hr | 245047.7 | 51320.2 | 161979.5 | 83059.9 | 8802.5 | 78540.4 | 89636.0 |
| Temperature ° C. | 100.0 | 59.6 | 158.8 | 40.0 | 30.0 | 36.8 | 102.8 |
| Pressure bar | 24.6 | 22.0 | 22.2 | 21.7 | 30.0 | 21.5 | 22.0 |
| Density kg/m³ | 492.8 | 38.2 | 440.5 | 508.6 | 779.1 | 39.8 | 549.1 |
| Molar wt. kg/kmol | 59.0 | 38.7 | 69.4 | 45.7 | 32.0 | 36.9 | 42.6 |

| Mass flow rate kg/hr | Stream number | | | |
|---|---|---|---|---|
| | 11 | 12 | 13 | 14 |
| MeOH | 28263.1 | 2243.3 | 7065.8 | 21197.3 |
| DME | 0.0 | 1104.0 | 0.0 | 0.0 |
| H2O | 2949.8 | 189.8 | 737.4 | 2212.3 |
| C2H4 | 0.0 | 0.0 | 0.0 | 0.0 |
| C3H6 | 0.0 | 358.5 | 0.0 | 0.0 |
| 1-C4H8 | 0.0 | 4971.4 | 0.0 | 0.0 |
| C—C4H8 | 0.1 | 2270.5 | 0.0 | 0.1 |
| T-C4H8 | 0.1 | 2942.5 | 0.0 | 0.1 |
| I—C4H8 | 0.0 | 4729.1 | 0.0 | 0.0 |
| C5H10 | 371.8 | 70.9 | 92.9 | 278.8 |
| Olefins C6-C8 | 28.8 | 0.0 | 7.2 | 21.6 |
| C2H6 | 0.0 | 0.0 | 0.0 | 0.0 |
| C3H8 | 0.0 | 4.5 | 0.0 | 0.0 |
| N—C4H10 | 0.0 | 11269.8 | 0.0 | 0.0 |
| I—C4H10 | 0.0 | 25647.1 | 0.0 | 0.0 |
| C5H12 | 1226.9 | 504.0 | 306.8 | 920.3 |
| Paraffins C6-C8 | 44.0 | 0.0 | 11.0 | 33.0 |
| Alcohols C2-C5 | 0.2 | 0.0 | 0.1 | 0.2 |
| Naphthenes C5-C6 | 5.2 | 0.0 | 1.3 | 3.9 |
| Aromatics | 0.4 | 0.0 | 0.1 | 0.3 |
| Ketones C3-C5 | 3.1 | 0.0 | 0.8 | 2.3 |
| Aldehydes C1-C3 | 424.4 | 0.0 | 106.1 | 318.3 |
| Methyl formate | 7.0 | 0.0 | 1.8 | 5.3 |
| H2 + CH4 | 0.0 | 0.0 | 0.0 | 0.0 |
| Mass flow rate kg/hr | 33325.0 | 56305.4 | 8331.3 | 24993.8 |
| Temperature ° C. | 119.4 | 53.3 | 40.0 | 40.0 |
| Pressure bar | 7.4 | 7.0 | 6.8 | 6.8 |
| Density kg/m³ | 668.5 | 543.3 | 773.8 | 773.8 |
| Molar wt. kg/kmol | 30.8 | 55.1 | 30.8 | 30.8 |

EXAMPLE 3

Configuration with solvent regeneration and circulation, with NMP/H$_2$O as solvent

| Mass flow rate kg/hr | Stream number | | | | | | |
|---|---|---|---|---|---|---|---|
| | 1 | 2 | 4 | 5 | 6 | 8 | 9 |
| MeOH | 408.2 | 98.9 | 0.0 | 408.2 | 0.0 | 0.0 | 507.1 |
| DME | 697.2 | 407.1 | 0.0 | 697.1 | 0.0 | 0.1 | 1104.2 |
| H2O | 765.5 | 161.8 | 0.0 | 765.4 | 0.0 | 0.0 | 4499.7 |
| C2H4 | 3819.6 | 8908.9 | 0.0 | 3818.7 | 0.0 | 12727.6 | 0.0 |
| C3H6 | 34975.6 | 25857.1 | 30.7 | 34940.9 | 0.0 | 60427.2 | 370.8 |
| 1-C4H8 | 7306.4 | 1440.0 | 3166.2 | 4140.0 | 0.0 | 0.0 | 5580.0 |
| C—C4H8 | 7541.2 | 963.3 | 5373.5 | 2167.7 | 0.0 | 0.0 | 3131.1 |
| T-C4H8 | 7483.5 | 1081.7 | 4773.3 | 2710.1 | 0.0 | 0.0 | 3791.8 |
| I—C4H8 | 7177.3 | 1416.4 | 3254.8 | 3922.3 | 0.0 | 0.0 | 5338.8 |
| C5H10 | 13626.8 | 266.3 | 13612.4 | 14.4 | 0.0 | 0.0 | 280.7 |
| Olefins C6-C8 | 10861.3 | 18.1 | 10861.3 | 0.0 | 0.0 | 0.0 | 18.1 |
| C2H6 | 144.0 | 271.7 | 0.0 | 143.9 | 0.0 | 415.7 | 0.0 |
| C3H8 | 549.3 | 360.4 | 1.6 | 547.6 | 0.0 | 894.4 | 13.6 |
| N—C4H10 | 23478.5 | 4035.8 | 13697.7 | 9780.3 | 0.0 | 0.0 | 13816.2 |
| I—C4H10 | 33454.3 | 7623.1 | 13344.2 | 20109.1 | 0.0 | 0.0 | 27732.2 |
| C5H12 | 55893.0 | 1272.8 | 55808.0 | 85.0 | 0.0 | 0.0 | 1357.8 |
| Paraffins C6-C8 | 18342.2 | 27.7 | 18342.2 | 0.0 | 0.0 | 0.0 | 27.7 |
| Alcohols C2-C5 | 297.8 | 0.1 | 297.8 | 0.0 | 0.0 | 0.0 | 0.1 |
| Naphthenes C5-C6 | 6203.3 | 4.1 | 6203.3 | 0.0 | 0.0 | 0.0 | 4.1 |
| Aromatics | 4277.7 | 0.3 | 4277.7 | 0.0 | 0.0 | 0.0 | 0.3 |
| Ketones C3-C5 | 396.1 | 1.4 | 396.1 | 0.0 | 0.0 | 0.0 | 1.4 |
| Aldehydes C1-C3 | 266.3 | 30.7 | 182.9 | 83.4 | 0.0 | 0.0 | 114.1 |
| Methyl formate | 94.9 | 2.6 | 94.8 | 0.0 | 0.0 | 0.0 | 2.7 |
| H2 + CH4 | 505.0 | 3552.5 | 0.0 | 503.7 | 0.0 | 4056.2 | 0.0 |
| NMP | 0.0 | 0.0 | 0.0 | 0.0 | 0.0 | 0.0 | 25000.0 |
| Mass flow rate kg/hr | 238565.0 | 57803.0 | 153718.0 | 84838.1 | 0.0 | 78521.2 | 92692.4 |
| Temperature ° C. | 100.0 | 77.4 | 164.5 | 48.4 | 0.0 | 37.6 | 157.9 |
| Pressure bar | 24.6 | 22.0 | 22.9 | 23.0 | 0.0 | 21.5 | 22.0 |
| Density kg/m$^3$ | 495.0 | 36.0 | 433.4 | 499.5 | 0.0 | 30.7 | 586.9 |
| Molar wt. kg/kmol | 59.4 | 39.6 | 70.1 | 46.5 | 0.0 | 36.9 | 57.5 |

| Mass flow rate kg/hr | Stream number | | | |
|---|---|---|---|---|
| | 11 | 12 | 13 | 14 |
| MeOH | 0.0 | 507.0 | 0.0 | 0.0 |
| DME | 0.0 | 1104.0 | 0.0 | 0.0 |
| H2O | 3571.4 | 928.2 | 0.0 | 3571.4 |
| C2H4 | 0.0 | 0.0 | 0.0 | 0.0 |
| C3H6 | 0.0 | 370.7 | 0.0 | 0.0 |
| 1-C4H8 | 0.0 | 5579.5 | 0.0 | 0.0 |
| C—C4H8 | 0.0 | 3130.8 | 0.0 | 0.0 |
| T-C4H8 | 0.0 | 3791.5 | 0.0 | 0.0 |
| I—C4H8 | 0.0 | 5338.3 | 0.0 | 0.0 |
| C5H10 | 0.0 | 280.7 | 0.0 | 0.0 |
| Olefins C6-C8 | 0.0 | 18.1 | 0.0 | 0.0 |
| C2H6 | 0.0 | 0.0 | 0.0 | 0.0 |
| C3H8 | 0.0 | 13.6 | 0.0 | 0.0 |
| N—C4H10 | 0.0 | 13815.0 | 0.0 | 0.0 |
| I—C4H10 | 0.0 | 27729.0 | 0.0 | 0.0 |
| C5H12 | 0.0 | 1357.7 | 0.0 | 0.0 |
| Paraffins C6-C8 | 0.0 | 27.7 | 0.0 | 0.0 |
| Alcohols C2-C5 | 0.0 | 0.1 | 0.0 | 0.0 |
| Naphthenes C5-C6 | 0.0 | 4.1 | 0.0 | 0.0 |
| Aromatics | 0.0 | 0.3 | 0.0 | 0.0 |
| Ketones C3-C5 | 0.0 | 1.4 | 0.0 | 0.0 |
| Aldehydes C1-C3 | 0.0 | 114.1 | 0.0 | 0.0 |
| Methyl formate | 0.0 | 2.7 | 0.0 | 0.0 |
| H2 + CH4 | 0.0 | 0.0 | 0.0 | 0.0 |
| NMP | 25000.0 | 0.0 | 0.0 | 25000.0 |
| Mass flow rate kg/hr | 28571.5 | 64114.5 | 0.0 | 28571.5 |
| Temperature ° C. | 178.2 | 41.2 | 0.0 | 179.4 |
| Pressure bar | 5.4 | 5.0 | 0.0 | 28.0 |
| Density kg/m$^3$ | 888.9 | 559.8 | 0.0 | 887.6 |
| Molar wt. kg/kmol | 63.4 | 55.3 | 0.0 | 63.4 |

The invention claimed is:

1. A process for removing oxygenates from mixtures of hydrocarbon compounds in which such oxygenates are present, wherein a liquid phase (1) containing hydrocarbons and oxygenates is charged to a first column (3), in which a light fraction comprising essentially all of the oxygenates contained in said liquid phase is separated as top product (5) by distillation and a heavier C4+ fraction essentially free of said oxygenates is separated as bottom product (4), the light fraction (5) and spatially separate therefrom a gaseous mixture of hydrocarbons and oxygenates (2) is charged to a second column (7), wherein the charging point of the gaseous mixture (2) is above the charging point of the light fraction (5) and wherein in column (7) a separation into a light and a heavy hydrocarbon fraction is effected by distillation, and a solvent (6) is supplied to the upper part of the second column (7), which dissolves the oxygenates and is discharged in the bottom product (9) of the second column, so that a hydrocarbon product (8) free of water and essentially free from oxygenates leaves the top of the second column (7), and a mixture of oxygenates, solvent and residual hydrocarbons (9) is withdrawn from the bottom of said second column (7).

2. The process as claimed in claim 1, wherein mono-alcohols or di-alcohols are used as said solvent.

3. The process as claimed in claim 1, wherein methanol, diethylene glycol, ethanol or propanol is used as said solvent.

4. The process as claimed in claim 1, wherein NMP (N-methylpyrrolidone) is used as said solvent.

5. The process as claimed in claim 1, wherein the second column (7) is operated at a pressure of 5 to 35 bar.

6. The process as claimed in claim 1, wherein the gas and liquid phases (2) and (1) originate from a catalytic reaction process.

7. The process as claimed in claim 1, wherein the mixture of oxygenates, solvents and residual hydrocarbons (9) withdrawn from the bottom of said second column (7) is supplied to a third column (10), a light fraction of hydrocarbons, oxygenates and DME (12) being withdrawn from the top of said third column (10), and regenerated solvent and water (11) is withdrawn from the bottom of said third column (10) and partly recirculated to the second column (7).

8. The process as claimed in claim 7, wherein a mixture of NMP and water is used as said solvent.

9. The process as claimed in claim 8, wherein the water content of said mixture is 5-20 wt-%.

10. The process as claimed in claim 9, wherein in said second column (7) the water content of the liquid phase is 0.5-2 wt-%.

11. The process as claimed in claim 10, wherein in said second column (7) the water content of the liquid phase is 1 wt. %.

* * * * *